(12) United States Patent
Miller et al.

(10) Patent No.: US 7,217,920 B2
(45) Date of Patent: May 15, 2007

(54) PANCAKE SPECTROMETER

(75) Inventors: Raanan A. Miller, Chestnut Hill, MA (US); Mark C. Terrell, Northborough, MA (US)

(73) Assignee: Sionex Corporation, Bedford, MA (US)

( * ) Notice: Subject to any disclaimer, the term of this patent is extended or adjusted under 35 U.S.C. 154(b) by 172 days.

(21) Appl. No.: 10/824,674

(22) Filed: Apr. 14, 2004

(65) Prior Publication Data

US 2004/0232325 A1 Nov. 25, 2004

Related U.S. Application Data

(63) Continuation of application No. 09/929,273, filed on Aug. 14, 2001, now Pat. No. 6,727,496.

(51) Int. Cl.
*B01D 59/44* (2006.01)

(52) U.S. Cl. .................. 250/287; 250/285; 250/286; 250/288

(58) Field of Classification Search ............ 250/287, 250/286, 288, 281, 282, 292, 285
See application file for complete search history.

(56) References Cited

U.S. PATENT DOCUMENTS

| | | | |
|---|---|---|---|
| 2,615,135 A | 10/1952 | Glenn, Jr. ............... | 250/41.9 |
| 2,818,507 A | 12/1957 | Britten .................. | 250/41.9 |
| 2,919,348 A | 12/1959 | Bierman ................ | 250/41.9 |
| 3,511,986 A | 5/1970 | Llewellyn ............... | 250/41.9 |
| 3,621,240 A | 11/1971 | Cohen et al. ............ | 250/41.9 |
| 3,931,589 A | 1/1976 | Aisenberg et al. ........ | 331/94.5 |
| 4,019,989 A | 4/1977 | Hazewindus et al. | 250/396 ML |
| 4,025,818 A | 5/1977 | Giguere et al. .......... | 315/337 |
| 4,136,280 A | 1/1979 | Hunt et al. .............. | 250/292 |
| 4,201,921 A | 5/1980 | McCorkle ............... | 250/493 |
| 4,315,153 A | 2/1982 | Vahrenkamp .......... | 250/396 R |
| 4,517,462 A | 5/1985 | Boyer et al. ............. | 250/286 |
| 4,761,545 A | 8/1988 | Marshall et al. ......... | 250/291 |
| 4,931,640 A | 6/1990 | Marshall et al. ......... | 250/291 |
| 5,019,706 A | 5/1991 | Allenmann et al. ....... | 250/291 |
| 5,298,745 A | 3/1994 | Kernan et al. ........... | 250/292 |

(Continued)

FOREIGN PATENT DOCUMENTS

RU 1405489 A1 6/1998

(Continued)

OTHER PUBLICATIONS

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

(Continued)

*Primary Examiner*—Hai Pham
*Assistant Examiner*—Lam S. Nguyen
(74) *Attorney, Agent, or Firm*—Fish & Neave IP Group Ropes & Gray LLP (57) ABSTRACT

Method and apparatus for identification of chemical compounds in a sample based on differences in ion mobility, wherein the filter and detector electrodes are formed radially spaced on facing substrates.

34 Claims, 8 Drawing Sheets

U.S. PATENT DOCUMENTS

| | | | |
|---|---|---|---|
| 5,420,424 | A | 5/1995 | Carnahan et al. |
| 5,455,417 | A | 10/1995 | Sacristan |
| 5,479,815 | A | 1/1996 | White et al. ................ 73/23.3 |
| 5,508,204 | A | 4/1996 | Norman ...................... 436/161 |
| 5,536,939 | A | 7/1996 | Freidhoff et al. |
| 5,559,327 | A * | 9/1996 | Steiner ........................ 250/292 |
| 5,654,544 | A | 8/1997 | Dresch ........................ 250/287 |
| 5,723,861 | A | 3/1998 | Carnahan et al. |
| 5,736,739 | A | 4/1998 | Uber et al. |
| 5,763,876 | A | 6/1998 | Pertinarides et al. |
| 5,789,745 | A | 8/1998 | Martin et al. |
| 5,789,747 | A * | 8/1998 | Kato et al. .................. 250/292 |
| 5,801,297 | A | 9/1998 | Mifsud et al. ............. 73/23.34 |
| 5,801,379 | A | 9/1998 | Kouznetsov |
| 5,834,771 | A | 11/1998 | Yoon et al. |
| 5,838,003 | A | 11/1998 | Bertsch et al. .......... 250/288 A |
| 5,965,882 | A | 10/1999 | Megerle et al. |
| 6,051,832 | A | 4/2000 | Bradshaw |
| 6,066,848 | A | 5/2000 | Kassel et al. ............... 250/288 |
| 6,107,624 | A | 8/2000 | Doring et al. ............... 250/286 |
| 6,124,592 | A | 9/2000 | Spangler ...................... 250/287 |
| 6,180,414 | B1 | 1/2001 | Katzman ...................... 436/181 |
| 6,323,482 | B1 | 11/2001 | Clemmer et al. ........... 250/287 |
| 6,495,823 | B1 | 12/2002 | Miller et al. ................ 250/286 |
| 6,504,149 | B2 | 1/2003 | Guevremont et al. ....... 250/286 |
| 6,512,224 | B1 | 1/2003 | Miller et al. |
| 6,540,691 | B1 | 4/2003 | Philips ........................ 600/532 |
| 6,618,712 | B1 | 9/2003 | Parker et al. ................. 706/15 |
| 6,621,077 | B1 | 9/2003 | Guevremont et al. ....... 250/292 |
| 6,639,212 | B1 | 10/2003 | Guevremont ............... 250/282 |
| 6,653,627 | B2 | 11/2003 | Guevremont ............... 250/288 |
| 6,680,203 | B2 | 1/2004 | Dasseaux et al. ............. 436/86 |
| 6,690,004 | B2 | 2/2004 | Miller et al. ................ 250/286 |
| 6,703,609 | B2 | 3/2004 | Guevremont ............... 250/287 |
| 6,713,758 | B2 | 3/2004 | Guevremont ............... 250/290 |
| 6,727,496 | B2 * | 4/2004 | Miller et al. ................ 250/287 |
| 6,753,522 | B2 | 6/2004 | Guevremont ............... 250/287 |
| 6,770,875 | B1 | 8/2004 | Guevremont ............... 250/288 |
| 6,774,360 | B2 | 8/2004 | Guevremont ............... 250/288 |
| 6,787,765 | B2 | 9/2004 | Guevremont ............... 250/288 |
| 6,799,355 | B2 | 10/2004 | Guevremont ............... 250/287 |
| 6,806,466 | B2 | 10/2004 | Guevremont ............... 250/287 |
| 2001/0030285 | A1 | 10/2001 | Miller et al. ................ 250/288 |
| 2002/0070338 | A1 | 6/2002 | Loboda ....................... 250/287 |
| 2002/0134932 | A1 | 9/2002 | Guevremont et al. ....... 250/281 |
| 2003/0020012 | A1 | 1/2003 | Guevremont et al. ....... 250/287 |
| 2003/0038235 | A1 | 2/2003 | Guevremont et al. ....... 250/287 |
| 2003/0052263 | A1 | 3/2003 | Kaufman et al. ............ 250/281 |
| 2003/0089847 | A1 | 5/2003 | Guevremont et al. ....... 250/282 |
| 2003/0132380 | A1 | 7/2003 | Miller et al. ................ 250/286 |
| 2004/0094704 | A1 | 5/2004 | Miller et al. ................ 250/287 |

FOREIGN PATENT DOCUMENTS

| | | |
|---|---|---|
| RU | 1412447 A1 | 6/1998 |
| RU | 1485808 A1 | 10/1998 |
| SU | 966583 | 10/1982 |
| SU | 1337934 A2 | 9/1987 |
| SU | 1627984 A2 | 7/1988 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 A1 | 2/2001 |
| WO | WO 01/22049 A2 | 3/2001 |
| WO | WO 01/35441 A1 | 5/2001 |
| WO | WO 01/69217 A2 | 9/2001 |
| WO | WO 01/69220 A2 | 9/2001 |
| WO | WO 01/69647 A2 | 9/2001 |
| WO | WO 02/071053 A2 | 9/2002 |
| WO | WO 02/083276 A1 | 10/2002 |
| WO | WO 03/005016 A1 | 1/2003 |
| WO | WO 03/015120 A1 | 2/2003 |

OTHER PUBLICATIONS

Barnett, D.A. et al., "Isotope Separation Using High-Field Asymmetric Waveform Ion Mobility Spectrometry," Nuclear Instruments & Methods in Physics Research (2000), pp. 179-185, 450(1).

Basile, F., "A Gas Sample Pre-concentration Device Based on Solid Phase Microextraction (SPME) and Temperature Programmed Desorption (TPD)," Instrumentation Sci. Tech., (2003), pp. 155-164, 31(2).

Carnahan, B. et al., "Field Ion Spectrometry—A New Technology for Cocaine and Heroin Detection," SPIE, (1997), pp. 106-119, 2937.

Demirev, P.A., et al., Microorganism Identification by Mass Spectrometry and Protein Database Searches, (1999), pp. 2732-2738, 74(14).

Demirev, P.A., et al., "Tandem Mass Spectrometry of Intact Proteins for Characterization of Biomarkers from *Bacillus cereus* T spores," Analytical Chem., (2001), pp. 5725-5731, 73(23).

Eiceman, G.A., et al., "Miniature radio-frequency mobility analyzer as a gas chromatographic detector for oxygen-containing volatile organic compounds, pheromones, and other insect attractants," J. Chromatography, (2001), pp. 205-217, 917.

Elhany, E., et al., "Detection of Specific *Bacillus anthracis* Spore Biomarkers by Matrix-Assisted Laser Desorption / Ionization Time-Of-Flight Mass Spectrometry," Rapid Commun. Mass. Spectrom., (2001), pp. 2110-2116, 15(22).

Fox, A., et al., "Determination of Carbohydrate Profiles of *Bacillus anthracis* and *Bacillus cereus* Including Identification of O-Methyl Methylpentoses Using Gas Chromatography-Mass Spectrometry," J. Clin. Microbiol. (1993) pp. 887-894, 31(4).

Guevremont, R. et al., "Atmospheric Pressure In Focusing in a High-Field Asymmetric Waveform Ion Mobility Spectrometer," Review of Scientific Instruments, (1999), pp. 1370-1383, 70(2).

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp. 10270-10277, 114(23).

Hathout, Y., et al., "Identification of *Bacillus* Spores by Matrix-Assisted Laser Desorption Ionization Mass Spectrometry," Appl. Environ Microbiol. (1999), pp. 4313-4319, 65(10).

Javahery, G. et al., "A Segmented Radiofrequency-Only Quadrupole Collision Cell for Measurements of Ion Collision Cross Section on a Triple Quadrupole," Mass Spectrometer, J. Am. Soc. Mass. Spectom., (1997), pp. 697-702, 8.

Krishnamurthy, T., et al., "Liquid Chromatography/Microspray Mass Spectrometry for Bacterial Investigations," (1999), pp. 39-49, 13.

Krylov, E.V., "A Method of Reducing Diffusion Losses in a Drift Spectrometer," Technical Physics, (1999), pp. 113-116, 4d(1).

Krylov, E.V., "Pulses of Special Shapes Formed on a Capacitive Load," Instruments and Experimental Techniques, (1997), pp. 628, 40(5).

Miller, R.A. et al., "A MEMS Radio-Frequency Ion Mobility Spectrometer for Chemical Agent Detection," (Jun. 2000) Proceedings of the 2000 Solid State Sensors and Actuators Workshop, Hilton Head, SC.

Miller, R.A. et al., "A MEMS radio-frequency ion mobility spectrometer for chemical vapor detection," Sensors and Actuators, (2001), pp. 301-312, A91.

Miller, R.A. et al., "A Novel Micromachined High-Field Asymmetric Waveform-Ion Mobility Spectrometer," Sensors and Actuators B, (2000) pp. 300-306, B67 (3).

Mowry, C., et al., "Rapid Detection of Bacteria with Miniaturized Pyrolysis-Gas Chromatographic Analysis," Proc. Of SPIE, (2001), pp. 83-90, 475.

Phillips, M., "Breath tests in medicine," Scientific American, (1992), pp. 74-79, 267(1).

Phillips, M., "Method for the Collection and Assay of Volatile Organic Compounds in Breath," Analytical Biochemistry, (1997), pp. 272-278, 247.

Pilzecker, P. et al., "On-Site Investigations of Gas Insulated Substations Using Ion Mobility Spectrometry for Remote Sensing of SF6 Decomposition," IEEE, (2000), pp. 400-403.

Riegner, D.E. et al., "Qualitative Evaluation of Field Ion Spectrometry for Chemical Warfare Agent Detection," Proceedings of the ASMS Conference on Mass Spectrometry and Allied Topics (Jun. 1997), pp. 473A-473B.

Schneider, A. et al., "High Sensitivity GC-FIS for Simultaneous Detection of Chemical Warfare Agents Mine," Safety Appliances Co., Pittsburgh, PA, USA, (2000), AT-Process, pp. 124-136, 5(3,4), CODEN: APJCFR ISSN: 1077-419X.

Shute, L.A. et al., "Curie-point Pyrolysis Mass Spectrometry Applied to Characterization and Identification of Selected *Bacillus* Species," J. General Micro., (JGMIAN) (1984), pp. 343-355, 130(2).

Viadyanathan, S., et al., "Flow-Injection Electrospray Ionization Mass Spectrometry of Crude Cell Extracts for High-Throughput Bacterial Identification," J. Am. Soc. Mass. Spectrom., (2002) pp. 118-128, 13.

Wang, Z., et al., "Mass Spectrometric Methods for Generation of Protein Mass Database Used for Bacterial Identification," Analytical Chem., (2002), pp. 3174-3182, 74(13).

Buryakov, I.A., et al., "A New Method of Separation of Multi-Atomic Ions by Mobility at Atmospheric Pressure Using a High-Frequency Amplitude-Asymmetric Strong Electric Field," *International J. Mass. Spectrometry and Ion Processes*, 128: 143-148 (1993).

Buryakov, I.A., et al., "Separation Ions According to Mobility in a Strong ac electric Field," *Sov. Tech. Phys. Lett.*, 17(6): 446-447 (1991). Appears to be English translation of attached Russian reference (Pisma v ZTF, v.17, N12, p. 60 (1991)).

Buryakov, I.A., et al., "Drift Spectrometer for the Control of Amine Traces in the Atmosphere," *J. Analytical Chem.*, 48(1): 156-165 (1993). Appears to be English translation of attached Russian reference (Zhurnal Anal. Chim., 48:N1, p. 156 (1993)).

Carnahan, B., et al., "Field Ion Spectrometry—A New Analytical Technology for Trace Gas Analysis," *ISA* Paper 96-009: 87-96 (1996).

Guevremont, Roger and Purves, Randy W., "High Field Asymmetric Waveform Ion Mobility Spectrometry-Mass Spectrometry: An Investigation of Leucine Enkephalin Ions Produced by Electrospray Ionization," *J. Am. Soc. Mass. Spectrom.*, 10: 492-501 (1999).

Handy, Russell, et al., "Determination of nanomolar levels of perchlorate in water by ESI-FAIMS-MS," *JAAS*, 15: 907-911 (2000).

Miller, R.A., et al., "A Novel Micromachined High-Field Asymmetric Waveform Ioon Mobility Spectrometer," Dept of Chem. And Biochem., New Mexico State University, Oct. 10, 1999.

Verenchikov, A.N., et al., Analysis ions in solutes by gaseous ion analyzer. "Chemical Analysis of the Environmental Objects," red. Malakhov. Novosibirsk, Nauka, pp. 127-134(1991).

Buryakov, I.A., et al., Devices and Methods of the Gaseous Electrophoresis. "Chemical Analysis of the Environmental Objects," red. Malakhov. Novosibirsk, Nauka, pp. 113-127 (1991).

I.A. Burykov, et al., "Device And Method For Gas Electrophoresis," *Chemical Analysis of Environment*, edit. Prof. V.V. Malakhov, Novosibirsk: Nauka, 1991, p. 113-127.

A.N. Verenchikov, et al., "Analysis Of Ionic Composition Of Solutions Using An Ion Gas Analyzer," *Chemical Analysis of Environment*, edit. Prof. V.V. Malakhov, Novosibirsk: Nauka, 1991, pp. 127-134.

Beverly, M.B. et al., "A Rapid Approach for the Detection of Dipicolinic Acid in Bacterial Spores Using Pyrolysis/Mass Spectrometry," Rapid Communications in Mass Spectrometry, Vo. 10, 455-458 (1996).

Dworzanski, J.P. et al., "Field-Portable, Automated Pyrolysis-GC/IMS System for Rapid Biomarker Detection in Aerosols: A Feasibility Study," Field Analytical Chemistry and Technology, vol. 1, No. 5, 295-305, (1997).

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

Krylova, N. et al., "Effect of Moisture on the Field Dependence of Mobility for Gas-Phase Ions of Organophosphorus compounds at Atmospheric Pressure with Field Asymmetric Ion Mobility Spectrometry," J. Phys. Chem. A, vol. 107, 3648-3654.

Snyder, A.P., "Detection of the Picolinic Acid Biomarker in *Bacillus* Spores Using a Potentially Field-Portable Pyrolysis—Gas Chromatography—Ion Mobility Spectrometry System," Field Analytical Chemistry and Technology, vol. 1, No. 1, pp. 49-58 (1996).

Thornton, S.N. et al., "Feasibility of Detecting Dipicolinic Acid in *Bacillus* Spores Using a Handheld IMS Device with Pyrolysis GC," Proceedings of the 1994 ERDEC Scientific Conference on Chemical and Biological Defense Research, Nov. 1994, Aberdeen Proving Grounds, MD, 1996, pp. 601-607.

Thornton, S.N. et al., "Pyrolysis-Gas Chromatography/Ion Mobility Spectrometry Detection of the Dipicolinic Acid Biomarker in *Bacillus subtilis* Spores During Field Bioaerosol Releases," Field analytical Methods for Hazardous Wastes and Toxic Chemicals: Proceedings of a Specialty Conference, Jan. 1997, Las Vegas, NV.

* cited by examiner

PANCAKE SPECTROMETER

RELATED APPLICATION

This application is a continuation of U.S. application No. 09/929,273, filed Aug. 14, 2001 now U.S. Pat. No. 6,727,496. The entire teachings of the above application are incorporated herein by reference.

BACKGROUND OF THE INVENTION

The present invention relates to chemical detection, and more particularly, to devices that enable analysis of compounds by high field asymmetric waveform ion mobility.

Spectrometers are used in chemical analysis for identification of compounds in a sample. These systems may take samples directly from the environment, or they may incorporate a front end device to separate or prepare compounds before analysis and detection. In some cases a quick indication of presence of particular compounds in a sample is needed, while at other times the goal is complete identification of all compounds in a chemical mixture.

The mass spectrometer is generally considered one of the most accurate detectors for compound identification. Mass spectrometers are expensive, easily exceeding $100K, and are difficult to deploy in the field. Mass spectrometers also suffer from the need to operate at low pressures, resulting in complex systems; mass spectrometers often require a highly trained operator and tend to require frequent maintenance. This presents a need for low cost, high quality, and compact chemical instruments that are capable of making a wide range of chemical identifications, as an alternative to a mass spectrometer.

There are several species of ion mobility spectrometer, all of which distinguish between chemical compounds based on ion mobility techniques. In a high field asymmetric waveform ion mobility spectrometer (FAIMS), ion filtering is achieved based on accentuating differences in mobility of ions of compounds being identified. The asymmetric field between the filter electrodes alternates between a high and low field strength that causes the ions to separate according to their mobility. Typically ion mobility in the high field differs from that in the low field. That mobility difference produces a net displacement of the ions as they travel in the gas flow through the filter. This results over time in a trajectory which, in absence of a compensation bias, causes the ions to hit one of the filter electrodes and to be neutralized. In the presence of a specific compensation bias, a particular ion species will be returned toward the center of the flow path and will pass through the filter without neutralization.

The amount of change in mobility between high field and low field and the amount of change in trajectory is compound-dependent. This permits separation of ions from each other according to their species by applying appropriately compensated filter drive signals.

In a typical FAIMS device, a gas sample, composed of a carrier gas and chemical compounds to be analyzed, is subjected to an ionization source and this ionized sample is carried by the carrier gas flow between the FAIMS filter electrodes. Application to the filter electrodes of a known asymmetric periodic voltage along with a known compensation bias, generates strong electric fields between the filter electrodes with the intent that selected ion species having a specific mobility in these known compensated high fields will flow through the FAIMS filter, if present in the sample, and these passed ions can then be detected and identified based on historical data for the device and with knowledge of the applied felds.

A planar FAIMS spectrometer with electrodes disposed over an essentially planar flow path has been disclosed which achieves a longitudinal flow and filtering of ions according to mobility differences. As well, a cylindrical FAIMS device with coaxial electrodes for longitudinal flow and filtering of ions according to mobility differences is disclosed in U.S. Pat. No. 5,420,424.

While the foregoing arrangements are adequate for a number of applications, it is still desirable to have a low cost and compact spectrometer that can render real-time or near real-time detection of chemical compounds, whether for the laboratory, the battlefield or in other environments, and whether as a stand alone detector or in cooperation with other devices such as a GC or an MS. It is also desirable to have a low-profile and portable spectrometer.

Furthermore, it is also desirable to have real-time or near real-time indication of compounds. This is important where fast indication is required to cooperate with fast sample input to the spectrometer, or possibly because of the dangers that arise from delay in detection of dangerous compounds in the environment. It is also desirable that the foregoing be achievable at low cost.

It is therefore an object of the present invention to provide a functional, small, low-cost spectrometer.

It is therefore an object of the present invention to provide a spectrometer with multiple flow paths that cooperate for fast and accurate sample processing and identification.

It is another object of the present invention to provide a chemical sensor that features the benefits of FAIMS and is able to operate rapidly, affording real-time or near real-time detection.

It is a further object of the present invention to provide a chemical sensor that features the benefits of FAIMS and can complete spectral scan in less than one second.

It is a further object of the present invention to provide a chemical sensor that features the benefits of FAIMS and is able to detect multiple ion species simultaneously.

SUMMARY OF THE INVENTION

The present invention provides a pancake FAIMS spectrometer with enhanced resolution and fast response time. The FAIMS apparatus and method provides for radial filtering and detection of selected ion species in a compact pancake package. The spectrometer of the invention is a simple and low cost device that nevertheless can perform substantive quantitative analysis of complex mixtures.

In practice of the invention, a sample containing a mixture of compounds is ionized in a chamber and then ion species representing the various compounds in the sample are passed to a FAIMS ion filter. Compensated FAIMS filter fields dictate passage through the filter of ion species of a certain mobility behavior and trajectory. The detector detects ions that have passed through the FAIMS filter.

In one embodiment of the invention, a pancake FAIMS spectrometer provides a radial system for identification of compounds in a carrier gas, the system having a pair of substrates mated facing each other to form at least one radial flow path. The substrates define at least one ion filter in the flow path with at least one filter electrode on each substrate facing each other across the flow path. The substrates further define at least one ion detector in the flow path. Ions representative of the compounds being carried in the carrier gas are flowed into the ion filter. Ions are passed by the ion filter according to ion mobility behavior. The carrier gas carries the passed ions to the detector located radially separate from the ion filter within the flow path for detection of the passed ion species.

It is a general principal in FAIMS operation that for a given electric field condition applied across the ion filter electrode pairs, only one species of ions, defined by ion mobility, makes it out the other end of the filter and into the detector. In practice of FAIMS spectrometers, the electric field required to allow the ions through the ion filter is dependent on the physical/chemical properties of the ions and the operational characteristics of the spectrometer. In general, a catalog of detection data for known compounds for the spectrometer can be generated and this knowledge can be used to operate the spectrometer and to enable identification of specific compounds in a sample. In general, as will be appreciated by a person skilled in the art, driver/controller must be enabled, such as with catalog information, and this may take the form of a look-up table in an on-board memory for a microprocessor part of the controller. In one use, a user might be interested in the presence of a certain species of compounds X, and might set driver/controller to run scan "X", which runs the filters through a range of compensated asymmetric fields and applies appropriate biases to the detector electrodes, to be able to detect the presence species X, in view of stored information in the look-up table, for example.

Embodiments of the invention provide a system for identification of compounds in a mixture based on ion mobility. The system includes at least a pair of substrates mated together facing each other over a gap. The substrates form at least one radial flow path in the gap. The ion filter electrodes on the substrates face each other over the gap and define at least one ion filter.

Ions representing compounds in the chemical mixture are filtered by the ion filter according to ion mobility characteristics as the ions travel radially along the flow path between the filter electrodes in the gap, with ion species having the mobility characteristics of interest passing radially through the filter.

Various embodiments of the invention are defined. The system may include wherein the filter filters ion species based on differences in ion mobility, wherein the substrates define at least one filter electrode on each substrate facing each other over the gap in the radial flow path, and wherein the flow path accommodates the flow of the ions, the ions traveling in the radial flow path between the filter electrodes, and selected species of the ions being passed by the ion filter according to differences in ion mobility behavior. The passed species travel radially in the flow path out of the filter for detection. A detector separate from the ion filter preferably performs ion detection.

In one embodiment, the gap is defined by a spacer. The spacer and the substrate surfaces define a plurality of radial flow paths, wherein the ions are introduced in the flow paths at one end thereof. Embodiments further feature a plurality of ion filters, wherein the filters filter ion species based on differences in ion mobility, wherein the substrates define a plurality of filter electrodes on each substrate facing each other over the gap in the radial flow path, and wherein the flow path accommodates flow of the ions, the ions traveling in the radial flow path between the filter electrodes, selected species of the ions being passed by the ion filters according to differences in ion mobility behavior, the passed species traveling radially in the flow path out of the filter for detection.

Embodiments may include a system drive-controller configured to apply a compensated asymmetric periodic voltage to each the ion filter electrode for generating fields across the gap, the ion filter filtering the ions according to their mobility in the fields.

Electrodes may be formed as rings on the substrates, enabling forming a plurality of filter and detector electrodes.

The substrates may be planar or non-planar. In one embodiment, the substrates define planar electrode-carrying surfaces facing each other across the gap, the substrates defining a detector in the radial flow path with at least one detector electrode on each substrate facing each other over the gap, wherein the filter electrodes are formed radially separate from the detector electrodes, wherein the electrodes are formed in arrays.

In other embodiments, the substrates define a plurality of electrodes, including detector electrodes and the ion filter having arrays of the electrodes as filter electrode pairs, further with a system drive-controller for generating fields at the filter electrode pairs across the gap, the ion filter filtering the ions according to their mobility in the fields. In one embodiment, each filter electrode is independently controlled by the drive-controller.

In an embodiment with a spacer, the gap is defined by the spacer and the substrate surfaces and the spacer define a plurality of radial flow paths. The array of filter electrodes, the detector electrodes, and the plurality of flow paths form a plurality of filter-detector combination paths. Each combination path is independently controllable by the drive-controller.

In practice of the invention, the flow paths are operable as a plurality of parallel ion filtering and detection paths for detection of a plurality of ion species simultaneously. Also, the electrode arrays may be formed as rings of electrodes on the substrate surfaces and the arrays may be formed as a series of unlike electrodes with differing filtering characteristics.

The detectors may include detector electrodes that are independent of each other, the driver-controller simultaneously outputting signals representing ion species detected on each of the detector electrodes independently.

In various embodiments, the substrates form electrode-carrying surfaces facing each other across the gap, the substrates mated together and forming an electronic spectrometer assembly. The substrates may be discrete ceramic substrates separated by a discrete spacer, mated with a bonding material to form the at least one flow path. In one embodiment the substrates are insulated disks, at least one of the substrates defining a central opening for forming an inlet for receipt of the compounds in the mixture under test. A collar seals the substrates at their outer circumference. The collar may include a port for the flow of carrier gas, with the substrates spaced apart to accommodate the flow.

In another aspect of the invention, the substrates form a housing, the filter and at least one flow path formed within the housing. The spacer cooperates with the substrates and the collar to define a plurality of enclosed flow paths in the housing. Preferably the substrates are insulated. The system has a system drive-controller which can be configured to apply a compensated asymmetric periodic voltage to each the ion filter electrode for generating fields across the gap, the ion filter filtering the ions according to their mobility in the fields, wherein the electrodes extend to contact pads accessible by the drive-controller.

Where ions are carried in a carrier gas flow, a pump is coupled to the substrates and communicates with the flow path for flow of ions through the filter electrodes.

In one embedment, a field asymmetric waveform ion mobility detection system has an input part and an output part, at least a pair of substrates defining between them at least one radial flow path for the flow of ions from the input part to the output part, a plurality of electrodes opposite each other and defined in the flow path, the plurality including at least one filter electrode ring array associated with each substrate, and an electronics part configured to apply controlling signals to the electrodes, the electronics part applying a compensated asymmetric periodic signal across the filter electrodes for changing the flow of ions in the flow path for filtering ion species.

In this embodiment, the electronics part may be further configured to sweep the applied controlling signals through a predetermined range according to the species being filtered.

Arrays of electrodes can form filter electrode pairs, and it is possible to adjust the filter pairs to filter desired ion species, or parts of a spectrum, according to an electronics control part configured to sweep controlling signals through a predetermined range according to the desired species to be filtered.

In another embodiment of the invention, an ion mobility spectrometer system includes a least two substrates joined together, the substrates defining a spectrometer housing having a sample inlet and a sample outlet, the housing forming at least one internal radial flow path connecting the sample inlet and sample outlet for the flow of ions to be filtered and detected, and an ion filter is disposed in the radial flow path and includes a pair of spaced filter electrodes for filtering of the ions in the flow path and radially passing ion species of interest for detection. In this system an array of electrode pairs can be provided wherein ones of the pairs have different filtering characteristics.

In another embodiment of the invention, a spacer is provided for establishing the gap and a collar is provided for joining the substrates at their outer circumference to close in the flow path.

An array of electrodes may form a ring of discontinuous electrodes. These may have various dimensions, such as rectangular or arcuate sectors formed on the substrates.

In some practices of the invention, the electrodes include electrical contacts for application of an asymmetric periodic voltage across the filter electrodes for controlling the filtering according to ion mobility. A control circuit can selectively adjusting a characteristic of the voltage, wherein the asymmetric periodic voltage is properly compensated, an ion species having a specified mobility characteristic can be passed through the filter for detection.

Ion flow may be slowed by forming an ion trap such as by forming a non-uniform spacing of the gap.

The radial flow of sample in the spectrometer of the invention enables simultaneous formation of many flow paths, depending upon the number of filter electrode pairs that have been formed on the substrates. Preferably each filter is formed with a filter pair. Any number of electrodes can be formed on the substrates. As a rough statement, preferably, if the number of flow paths is an integer I, the total number of filter electrodes is at least 2I.

The electrodes can be defined on the substrates as a plurality of electrode rings, and pairs of the rings forming ion filter electrodes. The rings can be formed with discontinuous electrode arrays. The electrodes may each have similar or dissimilar filtering characteristics.

Where a first set of rings forms the spectrometer filter, a second set of rings can be formed as detector electrodes. The rings can be formed with discontinuous electrode arrays. The electrodes may each have similar or dissimilar filtering characteristics.

In a further embodiment of the invention, a pair of substrates form a first filter stage, further comprising a second filter stage, wherein the ions filtered by the first stage are inputted to the second stage, and ions passed by the second stage are detected and identified according to species.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The present invention provides a low-profile spectrometer. Embodiments of the invention are volume-manufacturable and low-cost.

Figure 1:
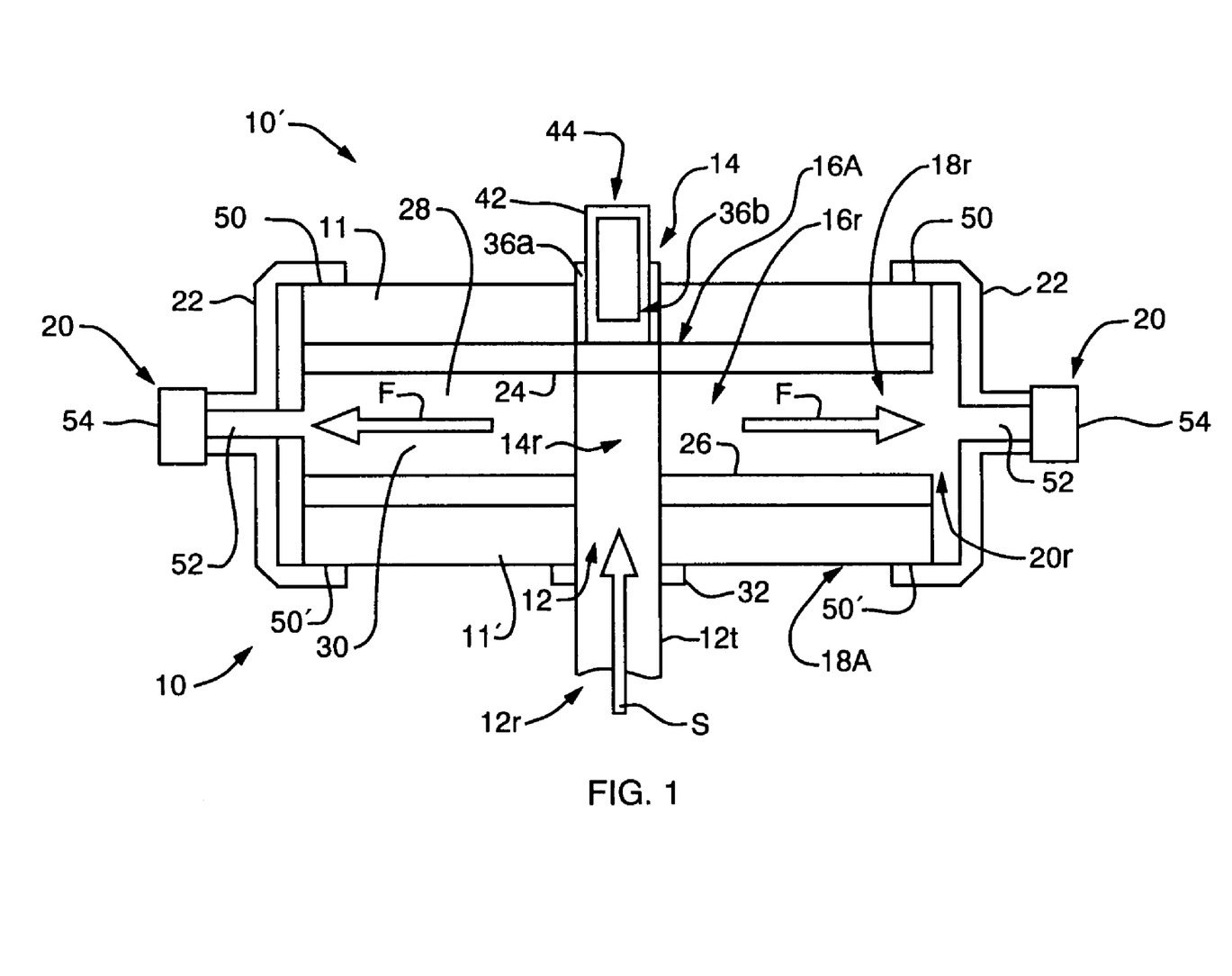
FIG. 1 is a side cross-section of one embodiment of the present invention.
Figure 2:
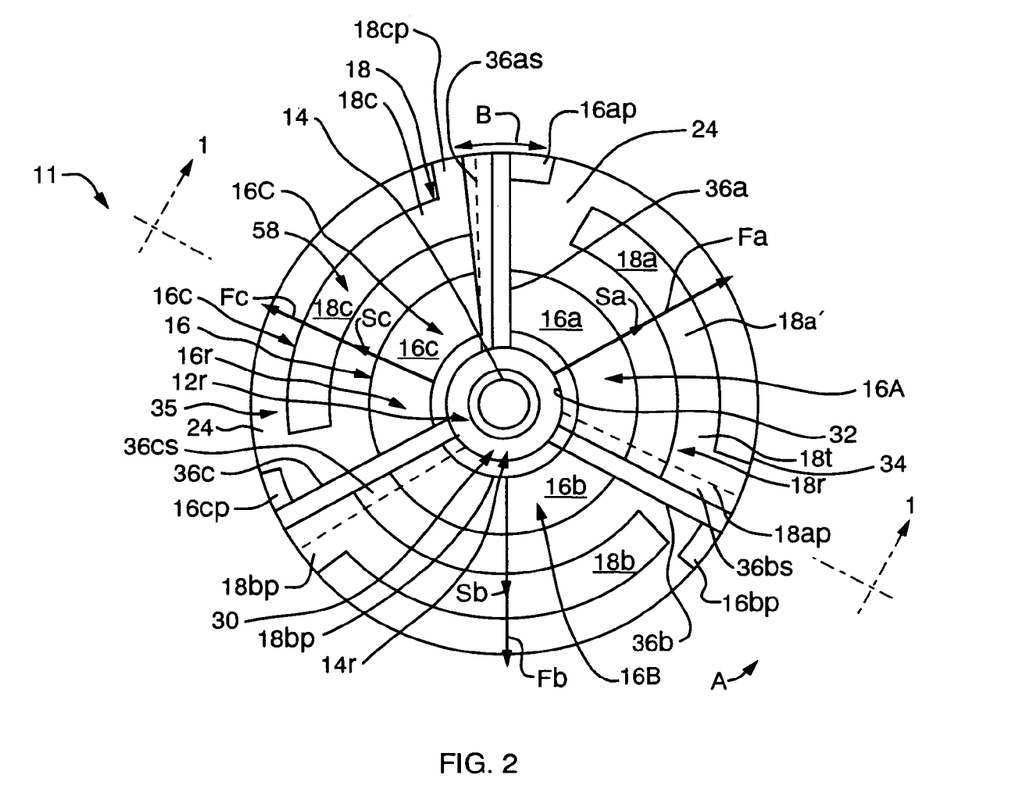
FIG. 2 is a plan view of the working surface of substrate 11 of the embodiment of FIG. 1; the view of substrate 11 in FIG. 1 is along line A—A of FIG. 2.

In an illustrative embodiment of the present invention, shown in FIGS. 1 and 2, a pancake FAIMS spectrometer 10 is formed by cooperation of a pair of disk-like substrates 11, 11'. The spectrometer includes a sample inlet 12, an ionization source 14, at least one ion filter 16A, at least one ion detector 18A, and a gas outlet 20. Substrates 11, 11' are mounted and contained within cylindrical collar or flange 22.

Referring to the plan view of working surface 24 of substrate 11 shown in FIG. 2, it will be appreciated that an opening 30 is formed at the center of substrate 11, defined by rim 32. Filter electrodes 16a, 16b, 16c are formed on surface 24 radially outward of rim 32. Each electrode independently extends out to a contact pad 16ap, 16bp and 16cp at the circumference 34 of the substrate, and may be driven together or independently. Detector electrodes 18a–c form a discontinuous ring 35 spaced radially outward of filter electrodes 16a–c. Each detector electrode extends out radially to a contact pad 18ap, 18bp and 18cp, adjacent to the substrate circumference 34, and may be driven together or independently. (It will be appreciated that while contact pads have been described herein, this is by way of illustration and not limitation. Other connection approaches are also within the spirit and scope of the invention including vias, whether radial or axial, for example.)

In the present illustrative embodiment, the working surface 26 of substrate 11' is identical to working surface 24 of Substrate 11. Substrates 11 and 11' are mated and spaced apart with some precision such that working surfaces 24, 26 form the operative sections of spectrometer assembly 10, by forming operational pairs of electrodes along parallel flow paths Fa, Fb, Fc. These operational pairs of electrodes include filter electrode pairs 16a—16a, 16b—16b, and 16c—16c, and detector electrode pairs 18a—18a, 18b—18b, and 18c—18c, on the respective cooperating working surfaces 24, 26.

It will be appreciated that these pairs of electrodes cooperate and are controlled to form working components of the spectrometer. For example, electrode 16a on substrate 11 faces electrode 16a of substrate 11' and together are driven to form FAIMS filter 16A, with filters 16B and 16C being similarly formed in this embodiment. Likewise, electrode 18a on substrate 11 faces electrode 18a of substrate 11' and together form a FAIMS detector 18A of the invention, with detectors 18B and 18C being similarly formed in this embodiment.

The operational regions of the spectrometer include a gas sample inlet region 12r, an ionization region 14r, an ion filter region 16r, an ion detector region 18r and a gas outlet region 20r, which are defined by and between the working surfaces 24 and 26 of substrates 11, 11' and collar 22, as assembled.

In this embodiment, gas sample S is flowed, as a carrier gas carrying compounds to be detected, from sample inlet region 12r to outlet region 20r, as parallel sample flows Sa, Sb, Sc along flow paths Fa, Fb, Fc, respectively, radially through filter region 16r and detector region 18r. In another embodiment, gas flow may be from outside to in, and still be within the spirit and scope of the invention.

In the embodiment of FIG. 1, inlet tube 12t is fitted into rim 32 of substrate 11'. Ionization source 14, such as an ultra violet photo-ionization lamp, is fitted into and hermetically sealed with rim 32 of substrate 11, located adjacent to ionization region 14r.

Figure 3:
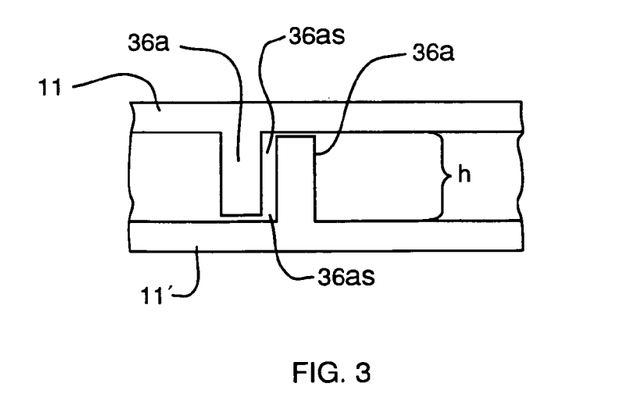
FIG. 3 is a side view showing cooperation of the spacers of the substrates in the embodiment of FIG. 1.

In this embodiment, spacer bars 36a–c are provided on working surface 24 of substrate 11, and extend radially between rim 32 and outer circumference 34, and working surface 26 of substrate 11' being identical. The substrates are mated together and precisely spaced apart by cooperation of the spacer bars. As shown in FIG. 2 by dotted outline adjacent to each of the spacer bars, a space 36as, 36bs, 36cs accommodates mating of the substrates together, enabling the spacers to be closely fitted. FIG. 3 shows the cooperating substrates 11, 11' with spacer bars 36a, 36a mated.

In this embodiment, the spacers are formed with uniform height "h" and therefore easily and precisely define the separation distance "h" of the working surfaces 24, 26, and thus the spacing and parallelism of the electrodes formed thereon.

In an alternative embodiment, the spacer bars 36a–c are not formed on the substrates. Instead, as shown in FIG. 4(A–E), a spacer part 40, formed as a ring 42 with extending spacer bars 44, is inserted to perform the spacing function. The spacer bars are formed having height "h", which defines the separation of the filter and detector electrodes.

The spacer part 40 is mounted between the substrates, with the substrate working surfaces 24, 26 supported against support surfaces 45 of spacer bars 44. In this embodiment, with spacer bars 36a–c not formed on the substrates, the spaces 36a–c now become double wide spaces on the substrate surfaces, such as space 36as' shown in FIG. 4D, for receipt of spacer bars 44.

Figure 4A:
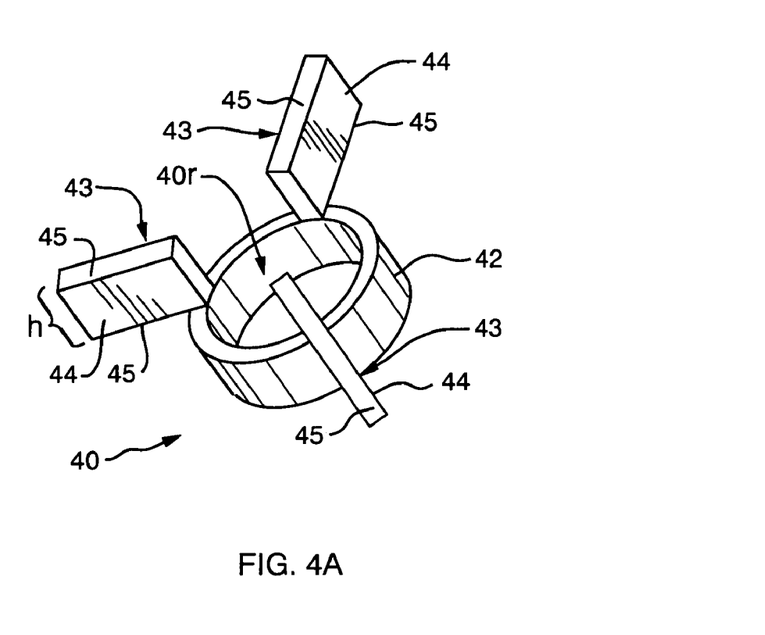
FIG. 4A is a perspective view of a spacer of the invention.
Figure 4B:
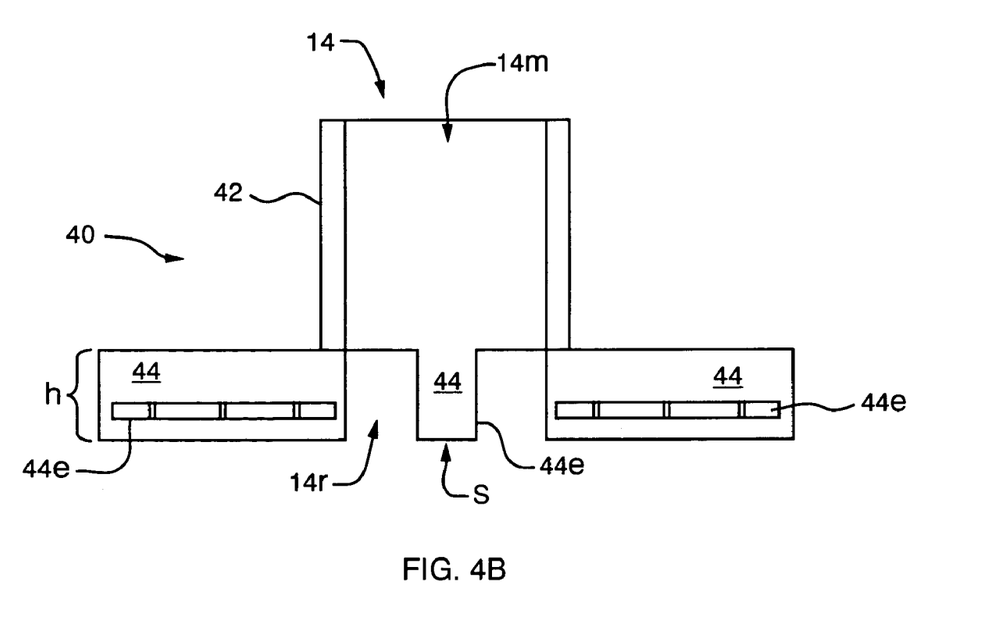
FIG. 4B is a side view of the spacer of FIG. 4A.
Figure 4C:
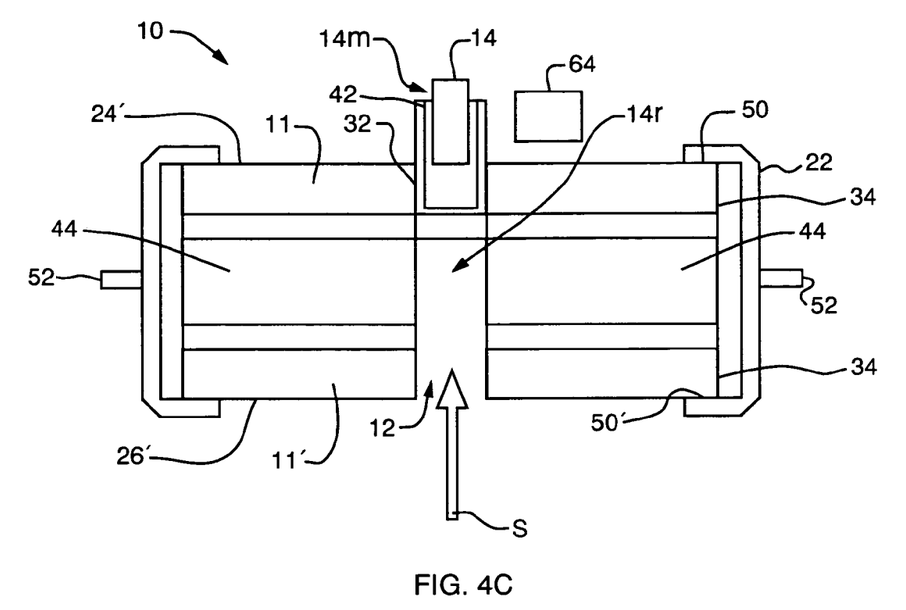
FIG. 4C is a side view of a spectrometer of the invention with the spacer of FIG. 4A mated between and with substrates 11, 11'.
Figure 4D:
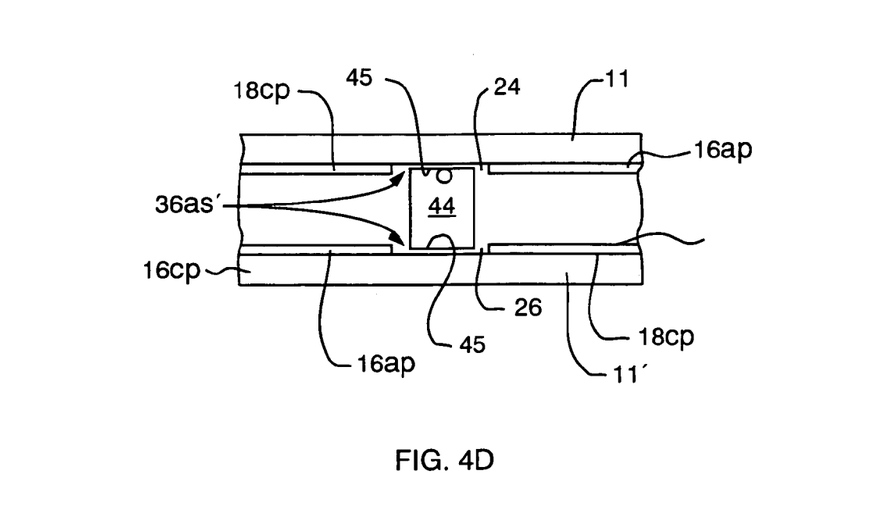
FIG. 4D is a side view showing cooperation of the spacers and the substrates in the embodiment of FIG. 4C.

Ring 42 is seated snugly within rim 32 of one substrate, such as substrate 11, and acts as a mount 14 m for mounting ionization source 14. An open region 40r is defined inside of where the spacer bars 44 descend from ring 42, leaving an open area that forms the ionization region 14r. In this embodiment, substrate 11 receives and is sealed at rim 32 to ring 42. Substrate 11' is joined to and sealed with the ring base 43.

In the disclosed embodiments, the cylindrical collar 22 is formed over the ends of substrates 11, 11', in any conventional bending or forming manner, whereby a hermetic seal is formed at joints 50, 50' where the substrates and collar meet. In general, the collar may be a discrete component or it may be formed as part of the spacer part 40 or as part of the substrates.

Figure 4E:
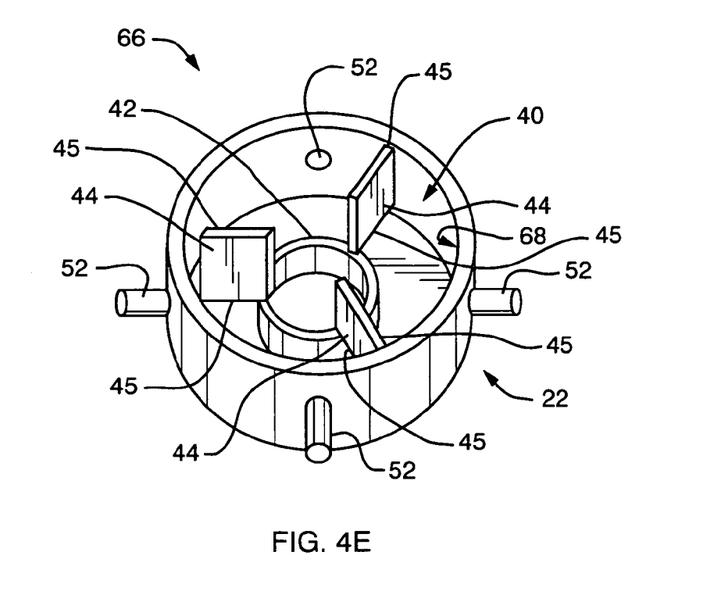
FIG. 4E is a perspective view of an alternative spacer assembly which also includes an outer collar.

In the further alternative embodiment of FIG. 4E, a single molded spacer collar combination part 66 defines both the spacer part 40 and the collar 22 as a single component. As above, the spacer part 40 is mounted between the substrates, with the substrate working surfaces 24, 26 supported against support surfaces 45 of spacer bars 44. The outer circumference 34 of the substrates mate against the inner circumference 68 of collar 22 and a hermetic seal is formed thereat.

Collar 22 provides one or several outlet tubes 52, 52 at outlet region 20r of spectrometer 10. A pump may be applied at the sample inlet 12, but more likely pump 54 is applied to the sample outlet tubes 52, 52 to create the gas flow through spectrometer 10.

In operation spectrometer 10, some ions will be driven into the filter electrodes and will be neutralized. These ions can be purged by heating. This heating may be accomplished in one embodiment by heating the flow path, such as by applying a current to filter electrodes, or to the spacers. For example, the spacers may include a heater electrode 44e shown in FIG. 4B. Such heating also can be used to heat and regulate the ion filter region in view of local temperature and humidity.

In operation of the illustrative embodiment of FIG. 1, a gas flow F is generated between the sample inlet 12 and gas outlet 20. Specifically, the gas sample S containing molecules of compounds to be detected is flowed into spectrometer 10 via inlet 12 and into ionization region 14r. The sample S is subjected to a strong source of ions (from ionization source 14) which puts molecules in the sample into a charged state. These ions are carried as gas samples Sa, Sb, Sc along the radial flow paths Fa, Fb, Fc into the ion filter region 16r. According to the asymmetric drive signal and compensation bias applied to the ion filter 16A, 16B, 16C, selected ion species will pass into the detector region 18r and will be detected, and then the carrier gas is exhausted via outlet tubes 52, 52.

In operation, adjustments are made to compensate the electric fields on the filters in order to filter a specific ion type of interest, depending upon the compensation signal applied. Ions that do not make it through the filter hit the ion filter electrodes and become neutralized. Once neutralized, these ions are not affected by the electric field and are carried out of the instrument by the carrier gas flow without being detected.

The ions that do make it through the filter with their charges intact, are detected as they strike and deposit their charges on the electrodes 18a, 18b, 18c that form detectors 18a, 18B, 18C. Any or all the detector electrodes may be used for such detection purposes. Alternatively, one detector electrode of each detector pair, for example detector electrode 18a on substrate 11, may be used as a deflector electrode 18a', to concentrate the detection signal onto the cooperating opposed detector electrode 18a on substrate 11', thus forming a detection electrode pair 18a–18a' with improved sensitivity.

Figure 5:
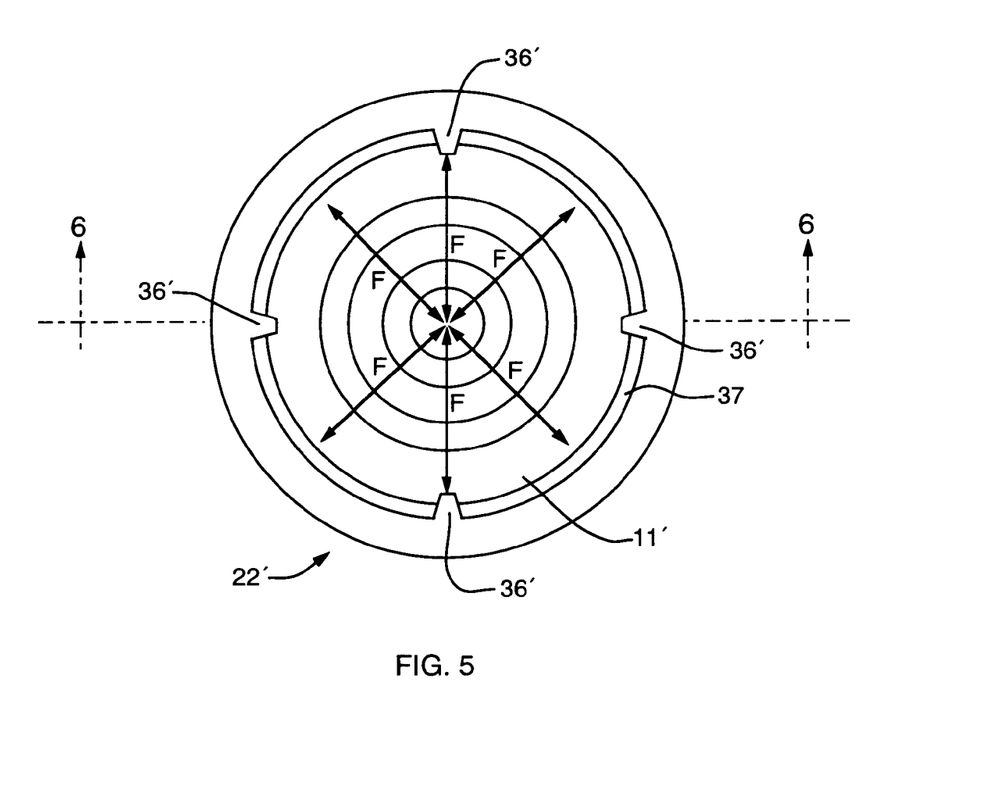
FIG. 5 is a plan view of the working surface of a substrate 11' of the invention mounted in an alternative collar-spacer of the invention.
Figure 6:
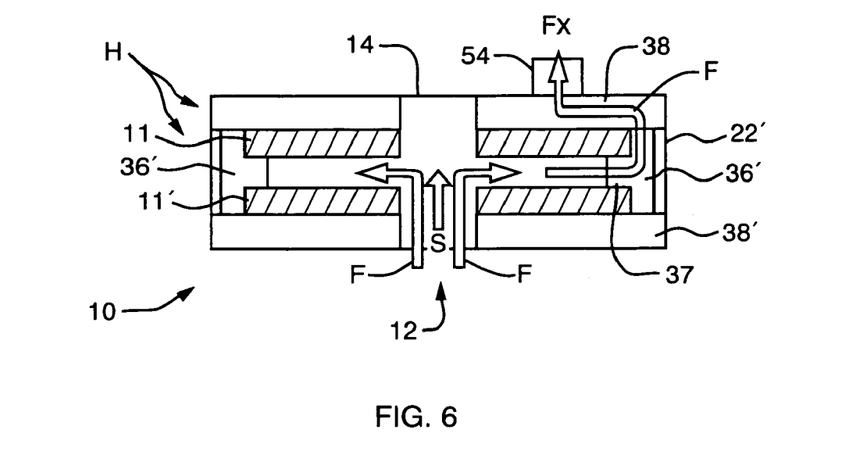
FIG. 6 is a side cross-section of an alternative spectrometer of the invention featuring the collar-spacer of FIG. 5 with mounted substrate 11', taken through line B—B, and with substrate 11 mounted thereto.

In another alternative embodiment of the invention, shown in FIGS. 5–6, the spacer and collar are integrated as collar 22', having spacer tabs 36' which perform the spacing function, but are at the end of the flow paths F and therefore do not interfere with the ion and carrier gas flow. Substrates 11, 11' are mounted on tabs 36' of Collar 22' with a gap 37 formed between the circumference of the substrates and the inside of the collar. An outer cover 38 is mounted within collar 22' over substrate 11 and an outer cover 38' is mounted within collar 22' over substrate 11'. The covers and collar cooperate to form a sealed housing H, with sample S entering through inlet 12 and flowing along flow paths F between the substrates, and then drawn out through gap 37 as exhaust Fx, exiting via pump 54.

Figure 7:
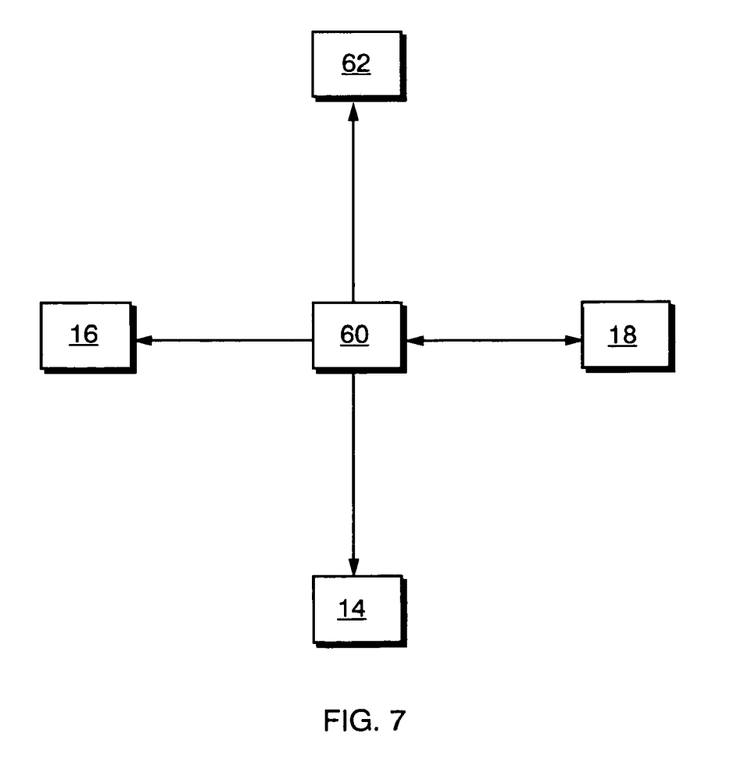
FIG. 7 is a schematic of the operating system of the present invention.

In practice of embodiments of the present invention, the gas flow, ionization, electric signals and filtering/detecting are under direction and control of system driver-controller 60, shown in FIG. 7. Driver-controller 60 drives the filter electrodes and biases the detector electrodes, with appropriate buffers, amplifiers and the like, and receives, interprets and enables display of detection data. In various embodiments, by applying or sweeping the field compensation over a predetermined range, the controller can generate a complete spectrum for ionized compounds in sample S. Detected signals are correlated with the applied bias and stored historical spectra data for device 10 to make a compound identification. Indication data is presented at system output 62.

Figure 8:
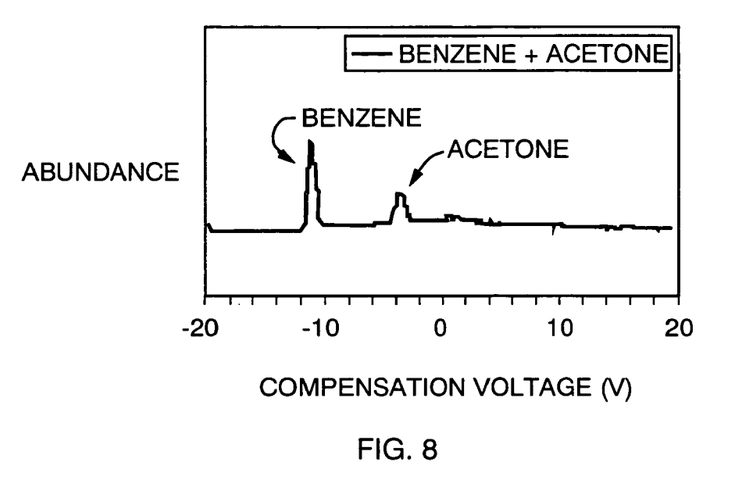
FIG. 8 is a plot showing spectra for a mixture of acetone and benzene, with the FAIMS filter compensation voltage swept from −20 volts to +20 volts.

As shown in FIG. 8, spectra for a mixture of acetone and benzene can be generated in practice of the invention, with individual peaks for acetone and benzene being separated and identified from the sample mixture. In one embodiment, the compensation voltage is swept from −20 volts to +20 volts to achieve this scan.

In practice of one embodiment of the invention, the asymmetric electric signal is applied in conjunction with a compensating bias voltage, and the result is that the filter passes a predicted ion species. In another embodiment, the asymmetric electric signal enables passing of the desired ion species where the compensation is in the form of variances in the duty cycle of the asymmetric electric signal, without the need for compensating bias voltage. Other variances in dimensions and electrical properties permit other compensation schema. As well, the detector electrodes, or electrode pairs, may be held at different potentials to broaden the range of detection, such as where each flow path Fa, Fb, Fc, etc., is tuned to a different portion of a spectrum of interest. In addition, the detector electrodes may be physically configured with different electrical properties or area dimensions that further enable manipulating the ions.

It will therefore be appreciated that spectrometer 10 can be operated in a number of different modes. In one mode, with Fn flow paths, the filter electrodes can be set at particular electric fields for a given flow path (F1–Fn) and the presence and concentration of species of ions can be continuously monitored at the detector electrodes. The advantage of this mode is that it requires a very simple data acquisition system and the response time of such a system can be very fast, around a millisecond or less. In a second mode, multiple ion species can be monitored, by changing electric field conditions. The control electronics and data readout are somewhat more complex, but multiple ion species can be detected rapidly. In a third mode, a complete spectra of the sample can be obtained. This is accomplished by sweeping the electric field conditions of each flow path, such as by sweeping the compensation voltage, over a large range. This produces a spectra with peaks corresponding to particular ion species present in the gas for each flow path that is scanned.

In practice of one embodiment of the invention, by sweeping the compensation bias over a predetermined voltage range, a complete spectrum for sample S can be achieved. By intelligent control of the system driver/controller 60 it is possible to select different operating regimes and as a result it is possible to allow ion species of interest to pass through the filter. In another embodiment, the compensation bias is in the form of varying electrical characteristics, such as the duty cycle of the asymmetric field, without the need for compensating bias voltage. This is supplied under direction and control of driver/controller. By means of these features, the apparatus is tunable, i.e., it can be tuned to pass only desired selected species according to mobility, trajectory and polarity, ion one or parallel radial flow paths.

The present invention may be used for simultaneous transport and detection of positive and negative ion species through each filter of the filter arrays in the parallel flow paths F. While multiple flow paths of the present invention enables each flow path to be tuned to pass different ions, still the ability to separate positive and negative ions in a single flow path affords an additional dimension of discrimination beyond compensation control alone. This makes possible identification of a wide range of compounds, including compounds that are difficult to identify by conventional means, all in a single spectrometer of the invention.

In one embodiment, positive and negative ions having the same mobility are passed through an ion filter in flow path F, and then these ions are detected by the two opposed detectors in each flow path, with one detector electrode being negatively biased and the other being positively biased in that flow path. The detected ions hitting each detector then are processed by driver-controller 60 to indicate the simultaneously detected compounds. If each flow path is tuned to a different spectrum, then a broad sample of compounds can be analyzed quickly and efficiently.

Because parallel radial flow paths are possible in practice of the invention, the filters may simultaneously pass different ion species (by control of the applied signals for each filter electrode pair). In addition, it is possible to sweep the control component for each filter pair over a voltage range for filtering a spectrum of ions. With an array of filters, a complete spectral range of compensation voltages can be more rapidly scanned than with a single filter pair. In an array configuration, each filter pair can be used to scan over a smaller voltage range. The combination of all of these scans results in sweeping the desired full spectrum in a reduced time period. If there are three filters, for example, the spectrum can be divided into three portions and each is assigned to one of the filters, and all three can be measured simultaneously. It will be appreciated that the number of filter and or detector pairs is by choice and is not limited to any particular number. In practice of the invention, the filter and detector arrays may include any number of electrodes depending on the size and use of the spectrometer.

The ion filter and ion detector of the invention may be formed with single electrode pairs (each electrode formed as continuous ring on the cooperating substrate surfaces 24, 26), although the electrodes are shown in FIGS. 1 and 2 as a circular array of filter electrodes and detector electrodes. In addition, serial arrays are also possible, such as having rings of filter electrodes, one after another in the radial flow paths.

Embodiments of the invention therefore may have various electrode arrangements, possibly including pairs, arrays and segments.

Thus operation of embodiments of the invention may include a single pair of filter and detector electrodes but performance may be enhanced by using an array of filters, detectors and flow paths, such as, for example, the filter array 16a–16c, and detector array 18a–18c, in flow paths Fa–Fc, as described above. It will be further appreciated that these multiple filters and detectors in parallel flow paths may be independently driven so as to be able to achieve a full spectral scan within a single detection cycle.

Any number of electrodes and arrays may be utilized in practice of the invention. In the illustrative embodiment of FIG. 9, eight electrodes E1–E8 are defined over four flow paths F1–F4, forming four filter-detector electrodes sets E1–E5, E2–E6, E3–E7, E4–E8. Within any of these sets, any electrode can be a filter or detector, adjusted for the particular scheme of sourcing of ions and direction of gas flow along the flow paths (i.e., flowing radially outside to inside or inside to outside, the inlet 12 and outlet 20 can swap roles). For example, an ionized sample might be drawn inward through ports 52 across the outer electrodes as filter electrodes, and then across the inner electrodes for detection before being vented at the open center 30 of the spectrometer. The flow can be pushed or pulled through the spectrometer such as with a pump.

Use of arrays is important when there is a desire to measure a number, perhaps even a dozen or so, compounds in a very short amount of time. Furthermore, if a fast GC is used as the front end to a FAIMS spectrometer, the widths of the chemical peaks eluting from the GC can be short. In order to obtain a complete spectral sweep over the required compensation voltage range in time to capture the information contained in the GC peal, the spectral range can be subdivided amongst the flow paths and ion filters in the array. This allows a simultaneous detection of all the constituents in the given GC peak in a shortened time frame.

In one mode, the filter array may include pairs of filter electrodes and may simultaneously enable detection of different ion species by applying a different compensation or bias voltage to each filter pair of the array, without sweeping. In this case, only an ion species that can be compensated by this fixed compensation voltage will pass through each filter, and the intensity will be measured.

Figure 9:
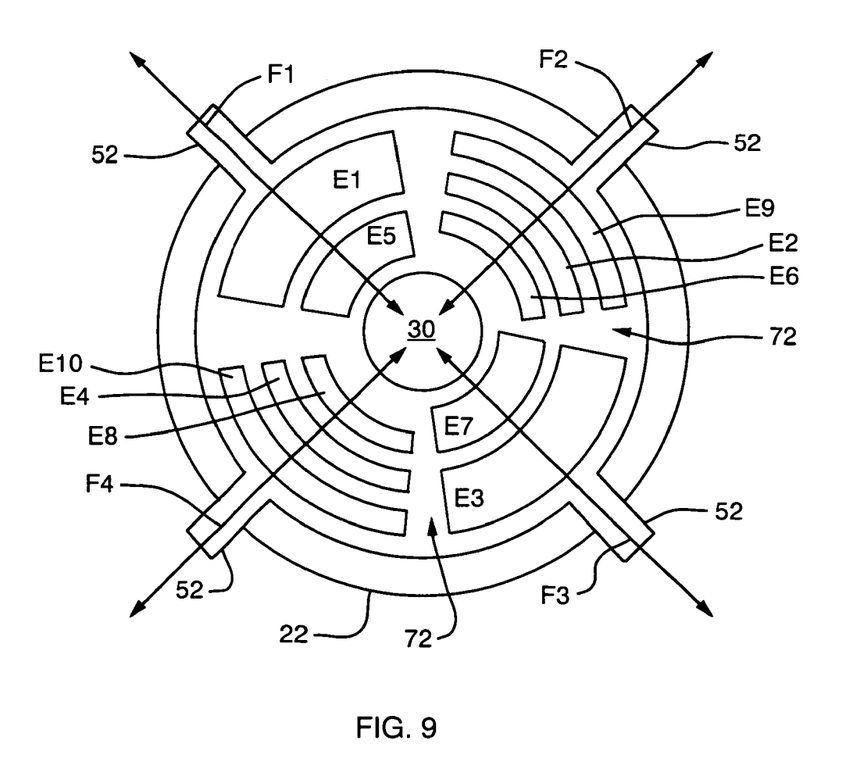
FIG. 9 is a plan view of an alternative multi-electrode embodiment of the invention, where electrodes of different sides and characteristic are presented on a single substrate of the present invention.

It will be further appreciated that a filter or detector array may also include a sequence of electrodes. For example, as shown in FIG. 9, of the three electrode set E6-E2-E9 (likewise E8-E4-E10) two of the electrodes may be driven to perform a sequence of filtering or detecting. With a sequence of filters/detectors, improved resolution and compound identification can be achieved.

It will be appreciated that the electrodes may be formed with the same or different physical or electrical characteristics, and the flow path itself may be planar or non-planar, with uniform or non-uniform spacing between the substrates and electrodes. These differences will effect ion travel time through the spectrometer as well as resolution and other filter and detector characteristics. As well, controller 60 may drive any electrode as desired for fixed filtering or scanned filtering. Furthermore, the electrodes themselves may be formed all the same or with different performance characteristics, such as shown in FIG. 9.

Figure 10:
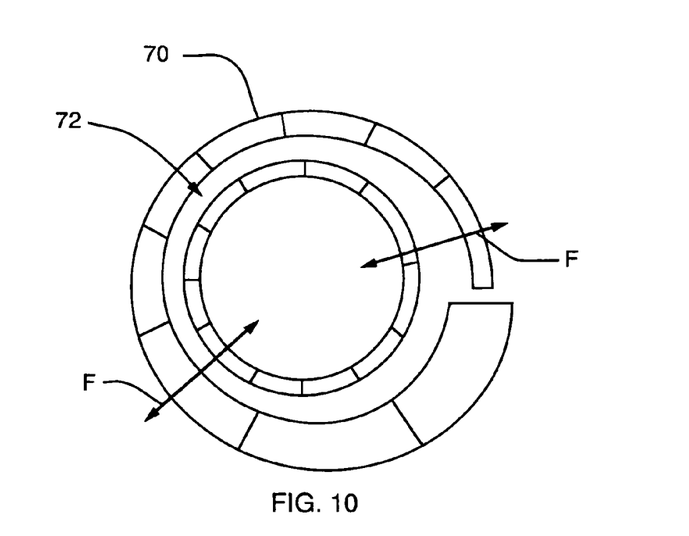
FIG. 10 is a plan view of a alternative electrodes in practice of the present invention.

FIG. 10 shows an example of two arrays of electrodes 70, 72. These arrays may or may not be formed together in a particular device and may be used as filter arrays or detector arrays. Ring array 70, is any array of electrodes, wherein each electrode is intended to have different physical/electrical characteristics. In one case the electrodes in the array vary in characteristic between low and high extremes, so that functionally each acts as if biased or compensated for operation in a small region of a spectrum of interest, when the asymmetric filter voltage is applied. It will be further appreciated that additively this array simulates a full electrical scan, and in this manner parallel flow paths (one flow path for each electrode of the array) can achieve a full scan in a shortened time frame. This is an example of a manufactured array which can be dedicated to a prescribed function, which is driven by a simplified driver/controller 60.

Meanwhile ring array 72 is shown with all the same electrodes. In this case, ion filtering will transpire entirely as controlled by driver/controller 60. This makes for a more versatile spectrometer. If sets of filter and detector electrodes between these rings each define separate flow paths, then each flow path can perform a part of an entire scan, driven by driver/controller 60, with appropriate compensated asymmetric signals being applied. The detection signals can be combined and correlated by driver/controller 60 to obtain a complete scan.

There foregoing invention achieves a simple, volume-manufacturable, low-cost spectrometer device that can perform fast and accurate scans, and with good resolution.

Figure 11:
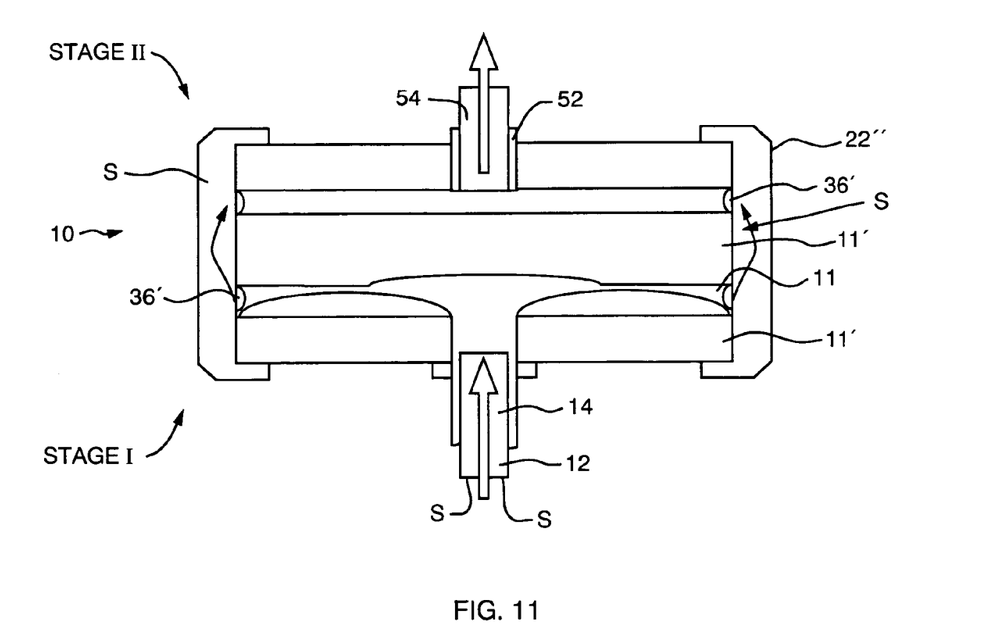
FIG. 11 is a side sectional view of two spectrometer modules whose flow paths are serially mated to form a multi-stage ion filter embodiment of the invention.

The spectrometer 10 is shown above as a single module, where multiple filtering and detection tasks can be performed in a single device. This arrangement is adequate for many applications. However, where the species that arrives at the detector region includes multiple compounds that cannot be easily differentiated by ion mobility, rather than performing detection at that moment, they can be passed along to a second filter process, more finely tuned to a narrower range or operating under a different regime, which may then be able to separate the otherwise unseparated compounds. An example of such multi-stage spectrometer is shown in FIG. 11, where Stage I, for example, may take the form of the FAIMS spectrometers described above, receiving a sample S at inlet 12, with ionization source 14 located here adjacent to inlet 12. The sample is filtered within Stage I and then is flowed into Stage II for final filtering. In this example the second stage filtering moves from the outer circumference inward to an outlet tube 52 and pump 54. This latter stage may be a FAIMS device or a shuttered IMS device, for example. Stages I and II are contained within a collar 22″ and spaced by spacers 36′. In a laboratory system, Stage I may be a FAIMS device and Stage II may be a mass spectrometer.

It will be further appreciated that embodiments of the invention feature a multi-functional use of substrates 11, 11′. These substrates are preferably made of insulating material such as glass, plastic, polymers or ceramic, and act as platforms for the definition and location of the component parts or regions of the device, in cooperation with a spacer and collar. The substrates, spacer and collar may all be formed as an integrated whole or a discrete parts and form a device housing 10′, enclosing the flow paths, filters and detectors. This multi-functional design reduces parts count while also precisely locating the component parts so that quality and consistency in volume manufacture can be achieved. As well, having optional identical working surfaces on the substrates, and the snap fit spacer 40, further enables cost-effective volume manufacture of an embodiment of the invention.

Spectrometer 10, with insulated substrate/flow path, achieves excellent performance in a simplified structure. The small size of the spectrometer 10 also provides unexpected improvements in performance and response time. Power requirements are reduced because of the reduced volume and size and shortened flow path. The use of an electrically insulated flow path also enables the applied asymmetric periodic voltage to be isolated from the detector electrodes. The result is a more sensitive spectrometer in a compact and low cost volume manufacturable package with good discrimination and fast response time. Sensitivity of parts per billion and parts per trillion can be achieved in practice of the invention.

It is also noted that use of the substrates as a support/housing does not preclude yet other "housing" features and functions. For example, collar 22′ and covers 38, 38′ enclose the substrates 11, 11′ and can provide a further hermetic seal that limits gas flow to the flow paths and flow of sample/gas at the inlet and outlet. As well, additional components, like batteries, can be mounted to the outside of the substrate/housing, e.g., in an enclosure adjacent to the ionization source 14. Furthermore, still other components can be on the housing surface, such as thermocouples, heaters, circuits, and the like.

Nevertheless, embodiments of the presently claimed invention stand over the prior art by virtue of performance and unique structure generally, as well as the substrate insulation function, support function, multi-functional housing functions, and in addition to the structure and features of spectrometer 10 discussed above.

Driver/controller 60 regulates the ion flow by controlling the ionization source and ion flow (e.g. a pump), and also regulates operation of the electrodes. In one practice of the invention, the asymmetric voltage applied to the ion filter electrodes ranges from about 900 to about 1.5 kV (high field condition), and a low voltage of about −400 to −500 V (low field condition). The frequency ranges 1–2 MHz and the high frequency has an approximate 30% duty cycle, although other operating ranges are possible. Amplifiers, such as Analog Devices model 459 amplifier, which exhibit linear response time and have a bandwidth of 7 ms and 140 Hz, respectively, may be used. The signal may be processed in a conventional manner, such as with a National Instruments board (model 6024E) to digitize and store the scans and with software to display the results as spectra, topographic plots or graphs of ion intensity versus time. The ionization source may be a radioactive source or a UV lamp, corona discharge, or the like.

It will now be appreciated that the present invention discloses method and apparatus for high field asymmetric waveform ion mobility spectrometry in a pancake device configuration. A preferred system includes an input section, an ion filter and detection section and a control section. Ideally ion filtering proceeds in a flow path under influence of high field asymmetric periodic signals, with detection integrated into the flow path, for producing accurate, real-time, data for identification of a broad range of chemical compounds.

Spacers can be used to fix the spacing between the electrodes on the substrates 11, 11′. While the substrates are shown above separated uniformly, it is also within the scope of the invention to have non-uniform spacing. For example, some electrodes may be closer together than others, or the substrates may be convex or concave, or other purposeful variations that impact on ion filtering and detection in spectrometer 10. For example, substrate 11 of Stage I in FIG. 11 is convex, or domed. This increased volume at the ionization region can act as an ion trap, slowing ion transit time and building up the sample to be filtered. This is particularly useful when inputs are rapid, such as will accommodate the output of a fast GC.

Whether the substrates of the invention have disk-like, rectangular or other surfaces, the flow paths herein are described as radial so as to distinguish from the axial flow path of cylindrical FAIMS devices and longitudinal flow paths of planar FAIMS devices. The present invention features a pancake spectrometer with radial flow paths, whether IMS or FAIMS or the like, and with substrates that may be uniform or non-uniform, arched, domed, skewed, canted, tilted or the like.

In the embodiment of FIG. 1, the substrates are shown as disks, but they also may be square, rectangular, or the like. Also in the embodiment of FIG. 1, the working surface 26 of substrate 11′ is identical to working surface 24 of Substrate 11. It will be further appreciated, however, that in other embodiments each working surface may have other or additional assets and features and may still be within the spirit and scope of the present invention. In alternative embodiments of the present invention, some or all of the substrate working surfaces and or of the electrodes may be bowed or otherwise non-planar and may or may not be parallel. These features enable sculpting or adjusting ion travel and behavior within flow paths of the invention.

The spacers of the invention may be formed as an extension of one of the substrates or as separate components, by etching or dicing silicon wafers or may be made of patterned Teflon, ceramic, or other insulators, or in any similar manner.

Other embodiments may have greater or fewer electrodes, depending upon a desired application, and still be within the spirit and scope of the invention. Various modifications of the specific embodiments set forth above are within the spirit and scope of the present invention. While a preferred embodiment of the invention is directed to essentially planar pancake FAIMS, other techniques of FAIMS or ion mobility or other discrimination techniques may also be practiced within the spirit and scope of the present invention.

Furthermore, having independent contact pads for each filter electrode enables each filter electrode to be driven independently to achieve a highly tuned apparatus with each flow path being independently controlled and driven, but this is an option and not essential to practice of the invention. Likewise, having independent contact pads for each detector electrode enables each detector electrode to be independently controlled and driven, but this too is an option and not essential to practice of the invention.

It will be appreciated that the terms detector, spectrometer and sensor may be used interchangeably for purposes of this disclosure within the spirit and scope of the present invention. The terms drift tube, flow channel and flow path may be used interchangeably and remain within the spirit and scope of the invention. The terms upper, lower, inner and outer are relative, and are used by way of illustration and not by way of limitation.

It will be further appreciated that the present invention is operable with liquid samples, such as by using electrospray, while for convenience the illustrative examples above describe operation of a gas sample however generated.

The examples and embodiments disclosed herein are shown by way of illustration and not by way of limitation. While a few electrodes or electrode rings or arrays of electrodes are shown in these illustrative embodiments, any practical number may be formed and used as the application demands. The scope of these and other embodiments is limited only as set forth in the following claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for analyzing one or more ion species of a sample, the system comprising,
   a first ion mobility filter associated with a first flow path for passing first ions of an ion species of the sample,
   a second ion mobility filter associated with a second flow path for passing second ions of the sample, the second flow path receiving the first ions from the first flow path,
   a third ion mobility filter associated with a third flow path for passing third ions of the sample, the third flow path receiving the first ions from the first flow path, and
   a first ion detector in the first flow path.

2. The system of claim 1, wherein the second ions include the first ions.

3. The system of claim 2, wherein the third ions include the first ions.

4. The system of claim 1, wherein at least one of the first, second, and third ion mobility filters includes a differential ion mobility spectrometer (DMS) filter.

5. The system of claim 1, wherein at least one of the first, second, and third ion mobility filters includes an ion mobility spectrometer (IMS).

6. The system of claim 1, wherein the first ion detector includes one or more electrodes.

7. The system of claim 6 comprising a second ion detector in the second flow path.

8. The system of claim 7, wherein the second ion detector includes one or more electrodes.

9. The system of claim 7 comprising a third ion detector in the third flow path.

10. The system of claim 9, wherein the third ion detector includes one or more electrodes.

11. The system of claim 1 comprising a fourth ion mobility filter associated with a fourth flow path for passing fourth ions of the sample.

12. The system of claim 11, wherein the first and fourth flow paths extend radially outward from a common ion inlet.

13. The system of claim 11 comprising a fourth ion detector in the fourth flow path.

14. The system of claim 13, wherein the fourth ion detector includes one or more electrodes.

15. The system of claim 11, wherein the fourth ion mobility filter includes at least one of an differential ion mobility spectrometer (DMS) filter and an ion mobility spectrometer (IMS).

16. The system of claim 11, wherein the first flow path and fourth flow path are the same flow path.

17. The system of claim 1 comprising a controller for automatically controlling at least one of the first, second, and third ion mobility filters.

18. The system of claim 1 comprising a mass spectrometer in fluid communication with the first flow path.

19. The system of claim 1 comprising a gas chromatograph for providing one or more ion species of the sample to the first flow path.

20. A method for analyzing one or more ion species of a sample, the system comprising,
    filtering first ions of a first ion species of the sample within a first flow path,
    filtering second ions of the sample within a second flow path, the second flow path receiving the first ions from the first flow path, and
    filtering third ions of the sample within a third flow path, the third flow path receiving the first ions from the first flow path, and
    detecting ions in the first flow path.

21. The method of claim 20, wherein the second ions include the first ions.

22. The method of claim 21, wherein the third ions include the first ions.

23. The method of claim 20, wherein filtering within one of the first, second, and third flow paths includes applying at least one asymmetric RF field.

24. The method of claim 20, wherein filtering within one of the first, second, and third flow paths includes applying a shuttered voltage gradient.

25. The method of claim 20 comprising detecting ions in the second flow path.

26. The method of claim 25 comprising detecting ions in the third flow path.

27. The method of claim 20 comprising filtering fourth ions of the sample within a fourth flow path.

28. The method of claim 27 comprising extending radially outward the first and fourth flow paths from a common ion inlet.

29. The method of claim 27 comprising detecting ions in the fourth flow path.

30. The method of claim 27, wherein the filtering includes at least one of applying an asymmetric RF field and applying a shuttered voltage gradient.

31. The method of claim 27, wherein the first flow path and fourth flow path are the same flow path.

32. The method of claim 20 comprising automatically controlling the filtering within at least one of the first, second, and third flow paths.

33. The method of claim 20 comprising flowing the first ions into a mass spectrometer.

34. The method of claim 20 comprising eluting the one or more ion species of the sample from a gas chromatograph.

* * * * *